US006897302B2

(12) United States Patent
Kowalczyk et al.

(10) Patent No.: US 6,897,302 B2
(45) Date of Patent: May 24, 2005

(54) METHOD FOR SYNTHESIZING
β-L-5-FLUORO-2',3'-DIDEOXY-2',
3'-DIDEHYDROCYTIDINE (β-L-FD4C)

(75) Inventors: Bo Kowalczyk, Orland Park, IL (US);
Zhao Lei, Naperville, IL (US); Ralph M. Schure, Darien, IL (US); Lisa Dunkle, Madison, CT (US)

(73) Assignee: Achillion Pharmaceuticals, Inc., New Haven, CT (US)

( * ) Notice: Subject to any disclaimer, the term of this patent is extended or adjusted under 35 U.S.C. 154(b) by 104 days.

(21) Appl. No.: 10/411,929

(22) Filed: Apr. 11, 2003

(65) Prior Publication Data

US 2004/0147479 A1 Jul. 29, 2004

(Under 37 CFR 1.47)

Related U.S. Application Data

(60) Provisional application No. 60/372,006, filed on Apr. 12, 2002.

(51) Int. Cl.$^7$ ...................... C07H 19/06; C07D 239/32; C07D 307/02
(52) U.S. Cl. ................... 536/27.11; 536/27.14; 536/28.4; 544/317; 544/320; 549/476
(58) Field of Search ................. 544/317, 320; 549/476; 536/27.11, 27.14, 28.4

(56) References Cited

U.S. PATENT DOCUMENTS

| | | | |
|---|---|---|---|
| 5,210,085 A | 5/1993 | Liotta et al. | 514/274 |
| 5,561,120 A | 10/1996 | Lin et al. | 514/49 |
| 5,627,160 A | 5/1997 | Lin et al. | 514/49 |
| 5,631,239 A | 5/1997 | Lin et al. | 514/49 |
| 5,703,058 A | 12/1997 | Schinazi et al. | 514/45 |
| 5,756,478 A | 5/1998 | Cheng et al. | 514/45 |
| 5,830,881 A | 11/1998 | Lin et al. | 514/45 |
| 5,869,461 A | 2/1999 | Cheng et al. | 514/43 |
| 5,905,070 A | 5/1999 | Schinazi et al. | 514/49 |
| 6,005,097 A | 12/1999 | Chen et al. | 536/27.11 |
| 6,280,940 B1 | 8/2001 | Potts et al. | 435/6 |
| 6,306,899 B1 | 10/2001 | Cheng et al. | 514/464 |
| 2002/0098202 A1 | 7/2002 | Wimmer et al. | 424/225.1 |
| 2002/0111313 A1 | 8/2002 | Campbell et al. | 514/18 |
| 2002/0147160 A1 | 10/2002 | Bhat et al. | 514/43 |

FOREIGN PATENT DOCUMENTS

| | | |
|---|---|---|
| WO | 92/14743 | 9/1992 |
| WO | 94/27616 | 12/1994 |
| WO | 97/47635 | 12/1997 |

OTHER PUBLICATIONS

Gulakowski, et al., "A Semiautomatic Multiparameter Approach for Anti–HIV Drug Screening," *Journal of Virological Methods*, vol. 33, pp. 87–100 (1991).

Elmore, et al., "The Human Epithelial Cell Cytotoxicity Assay for Determining Tissue Specific Toxicity," *Methods in Cell Science*, vol. 22, pp. 17–24, (2000).

Elmore, et al., "Comparative Tissue–Specific Toxicities of 20 Caner Preventive Agents Using Cultured Cells From 8 Different Normal Human Epithelia," in Vivo & *Molecular Toxicology*, vol. 14(3), pp. 191–207.

Lohmann, et al., "Replication of Subgenomic Hepatitis C Virus RNAs in a Hepatoma Cell Line," *Science*, vol. 285, pp. 110–113 (1999).

Mitsuya, et al., "3'–Azido–3'–dexoythymidine (BW A509U): An antiviral agent that inhibits the infectivity and cytopathic effect of human T–lymphotropic virus type III/ lymphadenopathy–associated virus in Vitro" *Proc. Natl. Acad Sci. USA*, vol. 82, pp. 7096–7100 (1985).

Mitsuya, et al., "Inhibition of the in vitro infectivity and cytopathic effect of human T–lymphotrophic virus type III/lymphadenopathy–associated virus (HTLV–III/LAV) by 2',3'–dideoxynucleosides" *Proc Natl. Acad. Sci USA*, vol. 83, pp. 1911–1915 (1986).

Mansuri, et al., "1–(2, 3–Dideoxy–β–D–glycero–pent–2–enofuranosy1) thymine. A Highly Potent and Selective Anti–HIV Agent" *J. Med. Chem.*, vol. 32, pp. 461–466 (1989).

Jeong, et al., "Asymmetric Synthesis and Biological Evaluation of β–L–(2E,5S)– and α–L–(2R,5R)–1,3–Oxathiolane–Pyrimidine and –Purine Nucleosides as Potential Anti–HIV Agents" *J. Med. Chem.*, vol. 36(2), pp. 181–195 (1993).

Lin, et al., "Rapid Communications: Antiviral Activity of 2',3'–Dideoxy– β–L–5–Fluorocytidine (β–L–FddC) and 2',3'–Dideoxy–β–L–Cytidine (β–L–ddC) Against Hepatitis B Virus and Human Immunodeficiency Virus Type 1 in Vitro" *Biochem. Pharmacol.*, vol. 47(2) pp. 171–174 (1994).

Lin, et al., "Design and Synthesis of 2',3'–Dideoxy–2', 3'–didehydro–β–L–cytidine (β–L–d4C) and 2',3'–Dideoxy–2',3'–didehydro–β–L–5–fluorocytidine (β–L–Fd4C), Two Exceptionally Potent Inhibitors of Human Hepatitis B Virus (HBV) and Potent Inhibitors of Human Immunodeficiency Virus (HIV) in Vitro" *J. Med. Chem.*, vol. 39(9), pp. 1757–1759 (1996).

*Primary Examiner*—Venkataraman Balasubramanian
(74) *Attorney, Agent, or Firm*—Wilmer Cutler Pickering Hale and Dorr LLP

(57) ABSTRACT

The invention provides a method of synthesizing β-L-5-fluoro-2',3'-dideoxy-2',3'-didehydrocytidine (β-L-FD4C). The method allows for large-scale production of β-L-FD4C in an efficient, cost-effective, and environmentally sound manner.

23 Claims, 1 Drawing Sheet

METHOD FOR SYNTHESIZING β-L-5-FLUORO-2',3'-DIDEOXY-2',3'-DIDEHYDROCYTIDINE (β-L-FD4C)

This application claims the benefit of provisional application No. 60/372,006, filed Apr. 12, 2002.

BACKGROUND

1. Field of the Invention

The invention relates to the preparation of nucleoside analogs for use as antiviral agents. In particular, the invention relates to the synthesis of β-L-5-fluoro-2',3'-dideoxy-2',3'-didehydrocytidine (β-L-FD4C).

2. Description of Related Art

Acquired immune deficiency syndrome (AIDS) caused by the human immunodeficiency virus (HIV) has created an international health crisis. According to the World Health Organization, by the end of the year 2001 an estimated 40 million people worldwide were living with HIV/AIDS. Approximately 5 million of these people became infected with HIV during 2001. HIV/AIDS is the fourth leading cause of death worldwide, resulting in 3 million fatalities in 2001 alone (*Weekly Epidemiological Record* 76:381–388 (2001)).

Another virus that poses a serious human health problem is the hepatitis B virus (HBV). Besides causing acute hepatitis, HBV can result in chronic infection leading to often-fatal cirrhosis and cancer of the liver. By the year 2000, a reported 2 billion people had been infected with HBV (*Fact Sheet WHO*/204, World Health Organization (October 2000)).

Various synthetic nucleosides have been identified as potential antiviral agents for treating HIV and HBV. Following the development of 3'-azido-3'-deoxythymidine (AZT) as an HIV therapy (Mitsuya et al., *Proc. Natl. Acad. Sci. USA* 82:7096–7100 (1985)), several 2',3'-dideoxy (dd) and 2',3'-didehydro-2',3'-dideoxy (D4) nucleosides were identified as potential HIV and HBV treatments. For example, nucleoside analogs approved for clinical use as antiviral agents included 2',3'-dideoxyinosine (ddI), 2',3'-dideoxycytidine (ddC) (Mitsuya et al., *Proc. Natl. Acad. Sci. USA* 83:1911–1915 (1986)), and 2',3'-didehydro-3'-deoxythymidine (D4T) (Mansuri et al., *J. Med. Chem.* 32:461–466 (1989)). While these nucleoside analogs are used in the form of the naturally-occurring "D" enantiomer, recent developments in the field have focused on several nucleoside analogs having the unnatural "L" configuration. For example, β-L-5-fluoro-2',3'-dideoxy-3'-thiacytidine (FTC) (Jeong et al., *J. Med. Chem.* 36:181–195 (1993)), β-L-5-fluoro-2',3'-dideoxycytidine (β-L-FddC) (Lin et al., *Biochem. Pharmacol.* 47:171–174 (1994)), and β-L-5-fluoro-2',3'-dideoxy-2',3'-didehydrocytidine (β-L-FD4C) (Lin et al., *J. Med. Chem.* 39:1757–1759 (1996)) have been identified as potential therapies for HIV and HBV.

β-L-FD4C has proven to be an especially promising antiviral agent for treating HIV and HBV (Lin et al., *J. Med. Chem.* 39:1757–1759 (1996)). Early synthetic methods for preparing β-L-FD4C (Lin et al., *J. Med. Chem.* 39:1757–1759 (1996)) suffered from low yield, and therefore were unsuitable for large-scale production. Alternative synthetic methods for preparing β-L-FD4C have been proposed (U.S. Pat. No. 6,005,097). However, a need exists in the art for new synthetic methods allowing for efficient, cost-effective, and environmentally sound commercial scale production of β-L-FD4C for use in treating the worldwide epidemics of HIV and HBV.

SUMMARY

The present invention addresses the above-mentioned need by providing new synthetic methods suitable for large-scale production of β-L-FD4C. The methods provide improved yield and efficiency along with reduced cost and environmental impact.

In one aspect, the invention provides methods of synthesizing β-L-5-fluoro-2',3'-dideoxy-2',3'-didehydrocytidine (β-L-FD4C). According to the methods:

(a) L-xylose of formula I

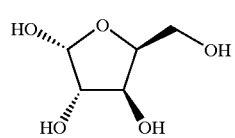

is reacted with acetone in the presence of a first acid catalyst and a dehydrating agent to afford a diacetal of formula II.

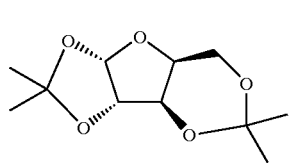

(b) The 2,3 acetal of the diacetal of formula II is hydrolyzed in the presence of a second acid catalyst to afford an acetal of formula III.

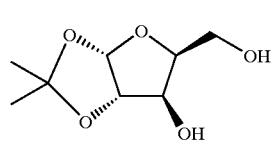

(c) The alcohol moieties of the acetal of formula III are acylated in the presence of a base catalyst to afford a diester of formula IV.

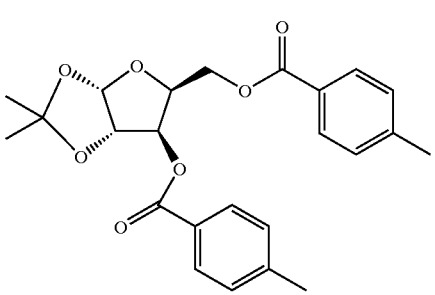

(d) The acetal moiety of the diester of formula IV is hydrolyzed in the presence of an acid to afford a diol of formula V.

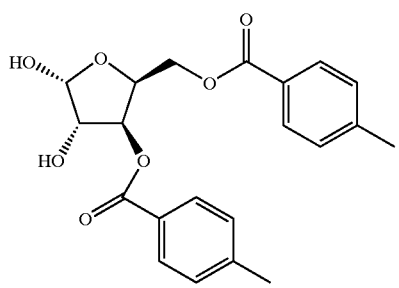

V (e) The hydroxyl groups of the diol of formula V are removed to afford a glycal of formula VI.

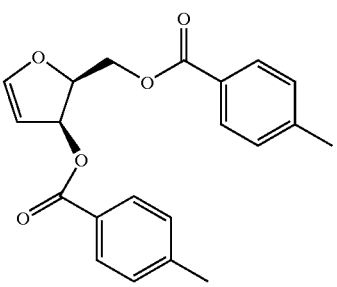

VI (f) 5-fluorocytosine of formula VII

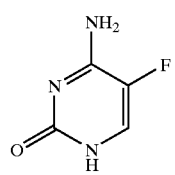

VII is bis-protected to afford bis-protected 5-fluorocytosine of formula VIII,

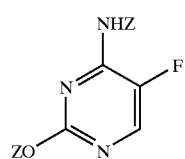

VIII wherein Z is a protecting group.

(g) The glycal of formula VI is coupled with the bis-protected 5-fluorocytosine of formula VIII in the presence of a halogenating agent to afford a halogenated cytosine derivative of formula IX.

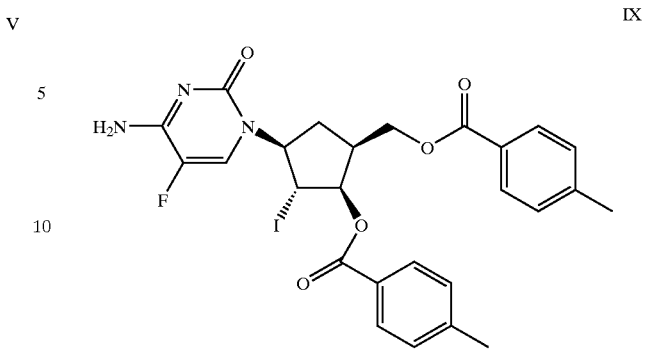

IX (h) The halogenated cytosine derivative of formula IX is treated with metallic zinc and acetic acid to afford a dideoxy, didehydro cytidine derivative of formula X.

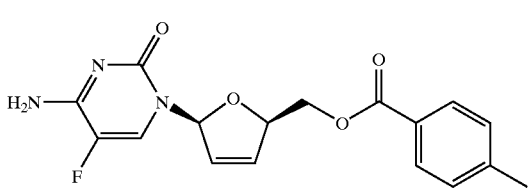

X (i) The ester moiety of the dideoxy, didehydro cytidine derivative of formula X is hydrolyzed in the presence of a base to afford β-L-5-fluoro-2',3'-dideoxy-2',3'-didehydrocytidine (β-L-FD4C) of formula XI.

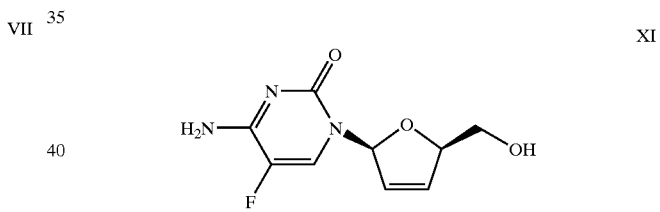

XI

BRIEF DESCRIPTION OF THE DRAWING

Certain embodiments of the invention are described with reference to the following figure, which is presented for the purpose of illustration only and is not intended to limit the invention.

DETAILED DESCRIPTION

Figure 1:
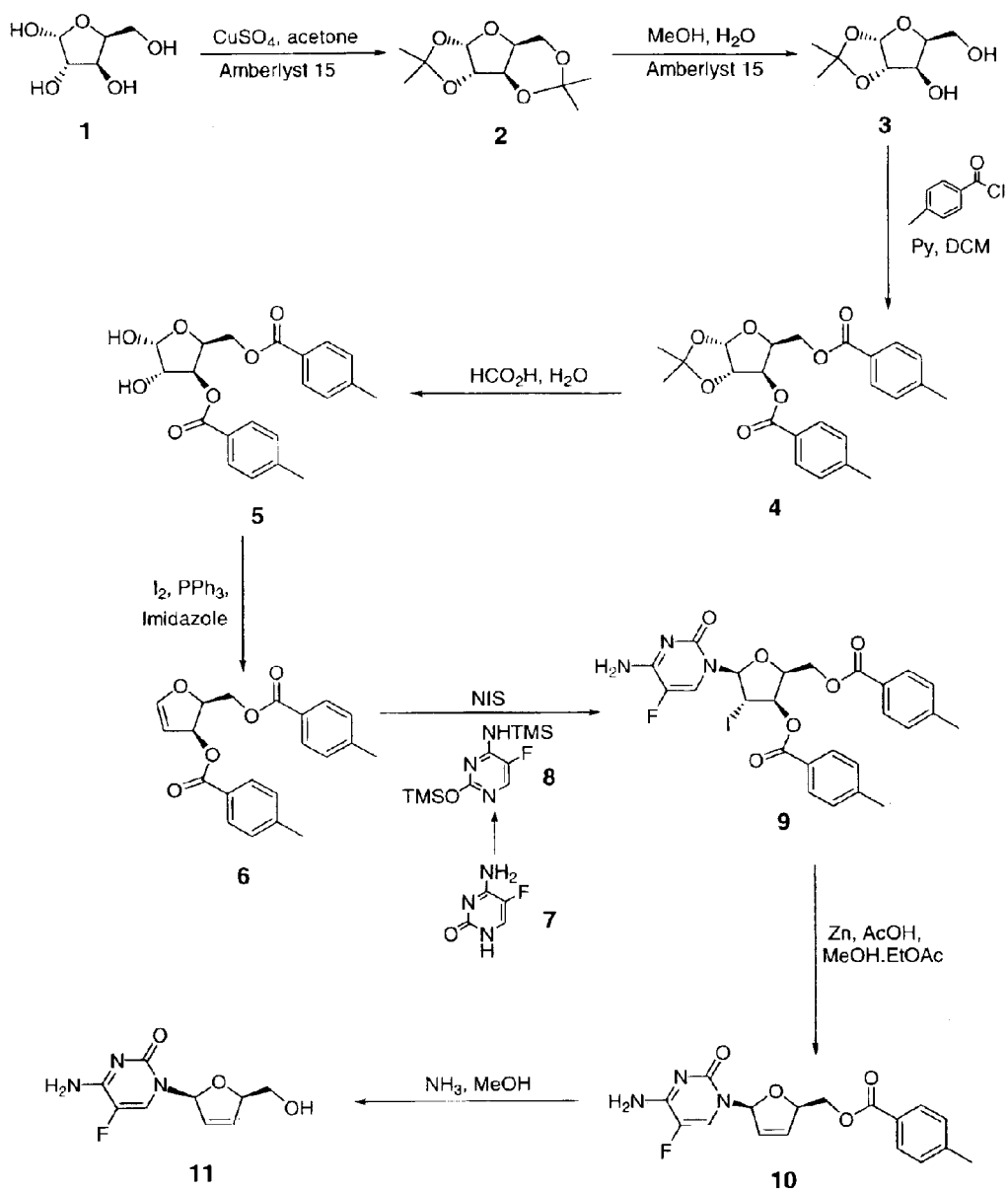
FIG. 1 illustrates a synthetic route for preparing β-L-FD4C according to certain embodiments of the invention.

The invention provides new methods for synthesizing β-L-FD4C and intermediates useful in the synthesis of β-L-FD4C. The methods allow for efficient, cost-effective, and environmentally sound large-scale production of β-L-FD4C with good yield and purity. The issued patents, published patent applications, and literature references cited herein are hereby incorporated by reference to the same extent as if each were specifically and individually indicated to be incorporated by reference. Any inconsistency between these publications and the present disclosure shall be resolved in favor of the present disclosure.

The term "lower alkyl," as used herein, means a straight chain or branched $C_1$–$C_4$ alkyl group, for example, methyl, ethyl, isopropyl, t-butyl, and the like. The term "acid catalyst," as used herein, refers to any acidic agent that catalyzes the desired chemical reaction. Non-limiting examples of acid catalysts for use in the synthetic methods described herein include inorganic acids, such as sulfuric acid or hydrochloric acid, and cation exchange resins. Cation exchange resins are insoluble acidic resins including, without limitation, sulfonated polystyrene resins, sulfonated polyfluorocarbon resins, and other cation exchangers on polystyrene, dextran, agarose, and the like. A "base catalyst" is any basic agent that catalyzes the desired chemical reaction. Non-limiting examples of base catalysts useful for the synthetic methods described herein include pyridine, triethylamine, and dimethylaminopyridine (DMAP). A "halogenating agent" is any agent capable of effecting halogenation, i.e., introduction of a halogen atom to a compound. A "dehydrating agent" is any agent that removes water. A "protecting group" is any group which when bound to one or more reactive sites on a compound prevents reaction from occurring at those sites, and which is removable from those sites by conventional chemical methods. A "derivative" or "analog" of a first compound is a second compound having a similar chemical structure to the first compound but lacking one or more functional groups or substituents or including one or more additional functional groups or substituents as compared to the first compound. The term "dideoxy" is used herein to describe a nucleoside moiety having a sugar group with a hydrogen instead of a hydroxyl group at each of two carbon atoms. The term "didehydro" is used to describe a nucleoside moiety having a sugar group that contains a double bond. For example, β-L-5-fluoro-2',3'-dideoxy-2',3'-didehydrocytidine (β-L-FD4C) has hydrogens in place of hydroxyl groups at the 2' and 3' carbons of the sugar moiety, and contains a double bond between those carbon atoms.

FIG. 1 illustrates a synthesis of β-L-FD4C according to certain embodiments of the invention. β-L-FD4C 11 is synthesized via a seven-step procedure using L-xylose 1 as the starting material. In at least some embodiments, synthesis of β-L-FD4C 11 is achieved from L-xylose 1 without evaporation to dryness of any of the intermediate compounds 2–10.

As shown in FIG. 1, the synthesis begins with the conversion of L-xylose 1 into the 1,2 protected acetal 3. This conversion is accomplished by preparing the diacetal 2 and then hydrolyzing the 3,4 acetal moiety in 2 under mild conditions to form the acetal 3. To form the diacetal 2, L-xylose 1 is combined with acetone, a dehydrating agent, and an acid catalyst. The dehydrating agent used in the synthesis shown in FIG. 1 is copper sulfate, which has been found to produce superior yields. Non-limiting examples of alternative dehydrating agents include $MgSO_4$ and $Na_2SO_4$. The acid catalyst used in the procedure illustrated in FIG. 1 is Amberlyst® 15 resin (strong acid macroreticular cation exchange resin with sulfonic acid functionality, Rohm and Haas, Philadelphia, Pa.). Such a resin catalyst is useful because it affords efficient reaction to form product with good purity, it is easy to handle and cost-effective, and it can be removed easily via filtration. Non-limiting examples of alternative resin catalysts include other cation exchange resins such as sulfonated polystyrene resins, sulfonated polyfluorocarbon resins, and other cation exchangers on polystyrene, dextran, agarose, and the like. Alternative non-resin acid catalysts for use in this reaction include, without limitation, sulfuric acid and hydrochloric acid.

Hydrolysis of the di-protected compound 2 to form the acetal 3 is effected by the addition of water in an organic solvent such as, for example, a lower alkyl alcohol, followed by the addition of an acid catalyst. In at least some embodiments, before this reaction is performed, the solution of 2 prepared from L-xylose 1 is neutralized to assure a successful change of solvent from acetone to lower alkyl alcohol or other organic solvent without degradation of 2 due to premature hydrolysis to form 3 or even convert back to xylose. Neutralization is accomplished by performing the solvent change in the presence of a base such as, for example, solid sodium carbonate. The solvent change allows the diacetal 2 to be used directly in the subsequent hydrolysis reaction to form the acetal 3, thereby increasing efficiency by eliminating the need for evaporation to dryness between reaction steps. In some embodiments, the solvent for the hydrolysis step is a lower alkyl alcohol such as, for example, methanol, as shown in FIG. 1; ethanol, which is less toxic; industrial methylated spirits (IMS), which is a cost-effective alternative to absolute ethanol for large-scale production; or a combination thereof. A non-limiting example of an alternative solvent is toluene. The acid catalyst used in the hydrolysis step as shown in FIG. 1 is Amberlyst® 15 resin. Alternative acid catalysts include, but are not limited to, other cation exchange resins, and inorganic acids, such as sulfuric acid or hydrochloric acid. The use of a non-resin catalyst reduces the environmental impact of the procedure by decreasing the amount of solid waste generated. Unwanted xylose in the resulting solution of acetal 3 is removed by trituration. Non-limiting examples of suitable solvents for trituration include tertiary butyl methyl ether (TBME), toluene/TBME, toluene/ethyl acetate, and dichloromethane (DCM)/ethyl acetate. Successful exchange into the trituration solvent is achieved without degradation of acetal 3 to xylose by performing the solvent exchange in the presence of a stabilizing base such as, for example, sodium bicarbonate. The use of a trituration solvent such as toluene/TBME that is also suitable for use in the next reaction step increases efficiency by allowing the solution of acetal 3 to be used directly in the next reaction step following trituration.

The alcohol moieties in compound 3 are acylated to form the corresponding ester moieties in compound 4 by treatment with an acid chloride such as, for example, p-toluoyl chloride, and a base catalyst. The synthesis illustrated in FIG. 1 employs pyridine as the base catalyst and DCM as the solvent for the reaction. Non-limiting examples of useful base catalysts include pyridine, triethylamine, dimethylaminopyridine (DMAP), and combinations thereof. Suitable solvents for use in performing the acylation reaction include DCM, toluene, TBME, and combinations thereof. Efficiency is improved by using a solvent such as, for example, toluene that is suitable for performance of the subsequent reaction step in order to avoid the need for evaporation to dryness between reaction steps. In some embodiments, in particular for large scale synthesis, use of more toxic materials such as pyridine and dichloromethane is limited to reduce the environmental impact of the procedure.

The 1,2 acetal group in compound 4 is hydrolyzed to afford the corresponding alcohol groups in compound 5. Hydrolysis is accomplished by administration of an acid such as, for example, formic acid or trifluoroacetic acid, in water. FIG. 1 illustrates hydrolysis using formic acid in water. Suitable solvents for performing the hydrolysis step include, without limitation, acetonitrile, toluene, and combinations thereof. In particular embodiments, formic acid in water is used with toluene/acetonitrile to afford a controlled homogenous reaction yielding the product diol 5 with good purity. In some embodiments, the product 5 is purified by trituration, for example, in hexane/TBME or toluene/TBME/heptane. In some alternative embodiments, a solvent exchange and precipitation from a solvent such as, for example, isopropyl ether is used to isolate the product diol 5 having enhanced purity.

The diol 5 is converted to the halogenated 5-fluorocytosine derivative 9 via a two-step coupling mechanism. First, diol 5 is converted to the glycal 6 by reaction with iodine, imidazole, and triphenylphosphine, as illustrated in FIG. 1. A non-limiting example of a suitable solvent for this reaction is dichloromethane. The resulting glycal 6 is stored under conditions designed to prevent degradation. Non-limiting examples of such conditions include storage below about 0° C. as a concentrated oil and storage at about 5° C. to about 6° C. in DCM or TBME for periods of up to about 3 days. In some embodiments, the resulting solution of 6 is used directly in the coupling step described below, thereby enhancing efficiency.

The coupling step that converts glycal 6 to the halogenated 5-fluorocytosine derivative 9 also requires bis-protected 5-fluorocytosine 8. FIG. 1 illustrates bis-protection of 5-fluorocytosine 7 with trimethylsilyl (TMS) groups to afford the bis-protected compound 8. Protection is accomplished by contacting compound 7 with 1,1,1-3,3,3-hexamethyldisilizane and a catalyst. In some embodiments, the catalyst is ammonium sulfate. Alternative protecting groups are well-known in the art and include, without limitation, dimethylhexylsilyl, t-butyldimethylsilyl, t-butyldiphenylsilyl, triphenylmethyl. Non-limiting examples of suitable solvents for use in the protection reaction include toluene, chlorobenzene, chloroform, dichloroethane, dichloromethane, isopropyl ether, and combinations thereof. In some embodiments, a solvent is used that is suitable for performance of the subsequent coupling reaction described below, and the solution of bis-protected 5-flurocytosine 8 is introduced directly into the coupling reaction. Performing the protection step in a solvent suitable for use in the subsequent coupling step, for example, chlorobenzene, dichloroethane (DCE), or dichloromethane (DCM), improves efficiency and product yield and quality by avoiding the need to isolate or evaporate to dryness the somewhat unstable product 8. In some embodiments, particularly for large-scale production, the use of more toxic solvents such as DCE and DCM is limited to reduce the environmental impact of the synthetic procedure.

Glycal 6 and bis-protected 5-flurocytosine 8 are coupled in the presence of a halogenating agent to produce the halogenated 5-fluorocytosine derivative 9. In some embodiments, the halogenating agent is N-iodosuccinimide (NIS), as illustrated in FIG. 1. In at least some embodiments, the coupling reaction is performed in a chlorinated solvent such as, for example, DCM, DCE, chlorobenzene, and combinations thereof. In some embodiments, use of DCE is avoided to decrease the environmental impact of the procedure. The product 9 is isolated from the chlorinated solvent by the addition of a lower alkyl alcohol, such as ethanol, which causes 9 to precipitate. Isolation of product 9 without the need for evaporation to dryness improves production time and avoids the need for prolonged heating of 9, which causes some degradation. Alternatively, product 9 is isolated by trituration with ethanol. In some embodiments, the product 9 is dissolved, for example, in a lower alkyl acetate, such as, for example, methyl acetate or ethyl acetate, for use in the subsequent reaction step. Adding a solution of 9 to the remaining reactants for the subsequent synthetic step avoids the need to add solid material to the reaction vessel.

As illustrated in FIG. 1, the halogenated 5-fluorocytosine derivative 9 is treated with metallic zinc and acetic acid to afford the dideoxy, didehydro 5-fluorocytidine derivative 10 via de-halogenation and elimination of toluic acid. The reaction is performed in an alcohol and an alkyl acetate. For example, a combination of a lower alkyl alcohol and a lower alkyl acetate is used, such as methanol and ethyl acetate, as shown in FIG. 1. In some embodiments, complicating trans-esterification reactions between the alcohol and the alkyl acetate are avoided by using an alcohol and an alkyl acetate having the same alkyl moiety, for example, methanol and methyl acetate, or ethanol and ethyl acetate. In some embodiments, the product 10 is isolated by trituration with a hexane/ethanol solution. Alternatively, acetone is added to the solution of product 10. The acetone removes trace amounts of the starting material 9 and toluoyl-related by-products, and also causes the product 10 to precipitate, thus allowing isolation of 10 without evaporation to dryness. The addition of acetone is preceded by aqueous washes, which are back-extracted to avoid loss of the water-soluble product 10.

The ester moiety of compound 10 is hydrolyzed to produce the final product β-L-FD4C 11. Suitable solvents for the hydrolysis reaction include, but are not limited to, polar alcohols, such as methanol. In at least some embodiments, hydrolysis is effected using a base. The base is present in a stoichiometric or catalytic amount. Non-limiting examples of useful bases include ammonia, sodium methoxide, potassium carbonate, 1,8-diazabicyclo[5.4.0]undec-7-ene (DBU), and isopropylamine. In the synthesis shown in FIG. 1, hydrolysis is performed using ammonia in methanol. In some embodiments, the use of ammonia gas is avoided to decrease the risk involved with handling toxic gases. Commercially available solutions of ammonia in methanol are useful, particularly in allowing subsequent isolation of the product β-L-FD4C 11 as a solid.

In at least some embodiments, the product β-L-FD4C is isolated. For example, the crude product 11 is purified using standard techniques known in the art, such as trituration, crystallization, and/or silica plug filtration. A non-limiting example of a useful purification procedure includes trituration in ethyl acetate or ethyl acetate/ethanol followed by column chromatography. Sometimes, particularly when the purity of crude β-L-FD4C 11 is below 95%, crystallization or silica gel filtration is used to obtain the desired product purity, despite the loss of some material through these methods. The quality of the product β-L-FD4C 11 is also enhanced by the use of purer starting material 10. Compound 10 exhibits more versatile solubility than β-L-FD4C 11. Thus, a wider range of purification procedures, including crystallizations, triturations, and/or silica plug filtrations, can be performed to increase the quality of the starting material 10, and thus indirectly improve the purity of the final compound β-L-FD4C 11.

In some alternative embodiments, β-L-FD4C 11 is isolated by the addition of a solvent that causes it to precipitate. Examples of suitable solvents for initiating precipitation of pure β-L-FD4C 11 include ethyl acetate and isopropanol. Precipitation of the final product β-L-FD4C 11 eliminates the need for evaporation to dryness and subsequent purification procedures. Avoiding silica gel chromatography is particularly desirable from an environmental standpoint, in order to reduce the volume of solvents used and the quantity of solid waste generated.

One of skill in the art will appreciate that the methods of the invention also are applicable in preparing compounds related to β-L-FD4C. Such related compounds include nucleoside analogs, for example, 2'3'-dideoxynucleosides or 2'3'-dideoxy-2'3'-didehydronucleosides having a purine or pyrimidine base attached to a ribose moiety. The pyrimidine base is a heterocyclic compound of the general class containing such compounds as uracil, thymine, cytosine, and related analogs. The purine base is a heterocyclic compound of the general class containing such compounds as hypoxanthine, xanthine, adenine, guanine, and analogs thereof. Non-limiting examples of purine or pyrimidine analogs include such bases having a CH moiety replaced by a nitrogen atom, and bases having one or more ring substituents incorporated, removed, or modified by conventional substituents known in the art, e.g., halogen, hydroxyl, amino, or $C_1$–$C_6$ alkyl. The methods of the invention also are useful for synthesizing the various synthetic intermediates described herein and analogs thereof.

The following non-limiting examples further illustrate certain embodiments of the invention:

EXAMPLE 1

β-L-FD4C was prepared according to the procedure illustrated in FIG. 1.

Preparation of Acetal 3

L-xylose 1 (1000 g, 6.66 moles, 1 eq), acetone (10 L), copper sulfate (1.33 kg, 8.3 moles, 1.25 eq), and Amberlyst® 15 resin (1000 g) were combined in a 22 L round bottom flask fitted with a mechanical stirrer, temperature probe, and nitrogen inlet/outlet. The reaction was stirred under nitrogen at room temperature for 16 hours. TLC (100% ethyl acetate, visualization with phosphomolybdic acid (PMA)) showed no starting material (Rf~0.05). 750 g of solid sodium carbonate was added and stirred for 30 minutes. The solution was filtered through Celite® (diatomite, World Minerals Inc., Santa Barbara, Calif.) to remove solids. The filtrate was concentrated to an oil under vacuum to yield 1.4 kg of a clear oil. $^1$H NMR confirmed absence of L-xylose 1. The oil was then dissolved in 7 L of a 4:1 methanol/water solution. While stirring, 1.4 kg of Amberlyst® 15 resin was added at room temperature. The solution was stirred at room temperature until TLC (100% ethyl acetate, visualization with PMA) showed the absence of di-protected xylose 2 (Rf~0.75). The solution was filtered and the filtrate was brought to pH 8 with solid sodium bicarbonate (approximately 20 g). The solvent was removed under vacuum at 50% to yield 1160 g of a light oil. The oil was triturated with 10 L of a 3:2 dichloromethane/ethyl acetate solution and dried over sodium sulfate. The dried solution was then filtered through Celite® and concentrated under vacuum to yield 1055 g (83%) of 3. $^1$H NMR and TLC confirmed structure.

Preparation of Diester 4

Acetal 3 (1050 g, 5.52 moles, 1 eq), pyridine (1800 mL, 23.18 moles, 4.2 eq), and dichloromethane (5.65 L) were combined in a 22 L round bottom flask fitted with an addition funnel, nitrogen inlet/outlet, temperature probe, mechanical stirrer, and ice bath. The solution was cooled to 5° C. with the ice bath while under nitrogen. p-Toluoyl chloride (1.76 kg, 11.48 moles, 2.08 eq) was added via the addition funnel while the temperature was maintained below 25° C. The solution was then allowed to stir for 16 hours under nitrogen. TLC (1:1 ethyl acetate/hexane, PMA visualization) indicated the reaction was complete. The solution was then washed with 1×5 L water, 1×5 L of a 3N HCl solution, 1×5 L water, and then dried over magnesium sulfate for three hours. After filtering off the drying agent, the filtrate was concentrated under vacuum to yield 2460 g (quantitative) of 4 as a light oil. TLC and $^1$H NMR confirmed product structure.

Preparation of Diol 5

9.3 L formic acid and 2 L water were combined in a 22 L round bottom flask fitted with a temperature probe, mechanical stirrer, and heating mantle. The diester 4 (2320 g, 5.44 moles, 1 eq) was dissolved in 2.3 L of acetonitrile and added in one portion to the formic acid/water solution. The combined solution was then brought to 50° C. and stirred for 2.5 hours. TLC (1:1 ethyl acetate/hexane, PMA visualization) indicated absence of starting material. The solution was then diluted with 6 L of saturated brine and extracted with 2×8 L dichloromethane (or 1,2 dichloroethane or chloroform). The combined dichloromethane layers were washed with 2×6 L water, 2×4 L saturated sodium bicarbonate (until pH was 7–8 by paper), 1×6 L water, 1×10 L brine, and dried over sodium sulfate. After removing the drying agent, the solvent was removed under vacuum to yield 1.88 kg (89%) of a light solid. The solids were then triturated with a 4:0.5 hexane/methyl tertiary butyl ether (MTBE) solution for 16 hours. The resulting white solids were isolated via filtration, washed with 2 L hexane, and dried in a vacuum oven at 35° C. to yield 1630 g (78%) of 5 as a light tan solid. The purity was 85% by HPLC and $^1$H NMR confirmed structure.

Preparation of Halogenated 5-Fluorocytosine Derivative 9

Bis-protected 5-fluorocytosine 8: Compound 8 was prepared as follows. 5-fluorocytosine 7 (605 g, 4.69 moles, 1.0 eq), 1,1,1-3,3,3-hexamethyldisilizane (5 L, 23.7 moles, 5 eq), and ammonium sulfate (24 g, catalyst) were combined under nitrogen in a clean, dry 12 L round bottom flask fitted with a mechanical stirrer, heating mantle, temperature probe, condenser, and nitrogen inlet/outlet. The solids dissolved after approximately 30 minutes at reflux, and the solution was heated at reflux for another 2 hours. The solution was allowed to cool to approximately 70° C. and was transferred under nitrogen to a rotovap. The solvent was removed under vacuum at 85° C. and azeotroped with 2×2 L anhydrous xylene to yield 8 as a white crystalline solid. The crystalline solid was dissolved in 6 L dichloromethane to form solution A, which was held until the coupling step.

Glycal 6: Compound 6 was prepared as follows. Dichloromethane (25 L), iodine (1985 g, 7.82 moles, 2 eq), triphenyl phosphine (2051 g, 7.82 moles, 2 eq), and imidazole (1170 g, 17.18 moles, 1.4 eq) were combined in a 100 L reactor fitted with cooling coils, nitrogen inlet/outlet, temperature probe, mechanical stirrer, and addition funnel. As the imidazole was added, the solution changed color from purple to yellow and the temperature rose to approximately 30° C. The solution was cooled to 15° C. under nitrogen. Compound 5 (1510 g, 3.91 moles, 1 eq) was dissolved in 10 L dichloromethane and added in portions to the 100 L reactor while the temperature was maintained below 20° C. After all of the 5 was added, the solution was stirred at room temperature for at least 2 hours. TLC (1:1 ethyl acetate/hexane, PMA visualization) after 2.5 hours showed absence of starting material (Rf~0.5), a slight spot at Rf~0.8 (intermediate), and product glycal 6 (Rf~0.9). The solution was quenched with 20 L of a 20% sodium thiosulfate solution and stirred for approximately 20 minutes. The layers were separated and the organic layer was washed with 1×20 L water, 1×20 L brine, and dried over magnesium sulfate for at least 1.5 hours. After removing the drying agent, the solution was concentrated to an oil under vacuum and triturated with 4 L of methyl tertiary butyl ether (MTBE). The solids (triphenyl phosphine oxide) were removed by filtration and washed with 3 L MTBE. The filtrate was concentrated to an oil under vacuum and stored under argon at −10° C. until the coupling step.

Coupling: The coupling step was performed as follows. Solution A from the 5-fluorocytosine protection reaction was added under nitrogen to a clean dry 22 L round bottom flask fitted with a mechanical stirrer, temperature probe, ice bath, and nitrogen inlet/outlets. The glycal 6 was dissolved in 7 L of dichloromethane and added to the 22 L round bottom flask. The combined solution was stirred under nitrogen while N-iodosuccinimide (NIS, 100 g, 4.88 moles, 1.25 eq) was added in portions. The temperature was held below 15° C. with the ice bath. After the NIS was added, the solution was allowed to stir at room temperature for at least 2 hours. TLC after 4 hours (1:1 ethyl acetate/hexane, PMA visualization) showed no glycal 6 (Rf~0.9), so the reaction was quenched with 1×20 L of 20% sodium thiosulfate. The solution was allowed to stir for approximately 20 minutes. As copious amounts of solids had formed, these were allowed to settle for 24 hours to facilitate filtration. The solids were removed by filtering through a 1 micron filter bag on a centrifuge. The filtrate was placed back into the 100 L reactor and the layers were separated. The organic layer was then washed with 1×20 L water, 1×20 L brine, and dried over sodium sulfate. After removing the drying agent, the dichloromethane was removed under vacuum to yield a dark oil. The oil was triturated with 4 L ethanol at 20° C. and stirred for 16 hours. The solids were isolated by filtration, washed with 4 L ethanol, and dried in the vacuum oven for 16 hours at 35° C. to yield 1259 g (53%) of 9 as an off-white solid. The purity was 98% by HPLC and $^1$H NMR confirmed product structure.

Preparation of Dideoxy, Didehydro Cytidine Derivative 10

Two separate runs were performed as follows.

Run 1: Compound 9 (935 g, 1.544 moles, 1 eq.), ethyl acetate (8.4 L), methanol (1 L), and acetic acid (93 mL, 1.544 moles, 1 eq) were added to a clean, dry 22 L round bottom flask. The solution was stirred for 10 minutes and zinc (200 g, 3.08 moles, 2.0 eq) was added in one portion. The temperature rose from 15° C. to 23° C. over 15 minutes. TLC (9:1 ethyl acetate/methanol, PMA & UV visualization) showed no reaction. One more equivalent of zinc (100 g) was added in one portion and the temperature rose to 41° C. over 15 minutes. TLC showed the reaction was complete within 30 minutes. The reaction was allowed to stir for 16 hours (overnight) at room temperature. The zinc was removed via filtration and the filtrate was washed with 1×10 L water and 1×10 L of a 10% ammonium chloride solution. The ethyl acetate was then concentrated to 1.5 L under vacuum and the resulting slurry was allowed to stir overnight at room temperature. The solids were isolated by filtration, washed with 1 L ethyl acetate and dried in a vacuum oven for 16 hours at 35° C. to yield 275 g (52%) of 10 as a white solid. The purity was 98% by HPLC and $^1$H NMR confirmed product structure. Attempts to obtain more compound from the mother liquor were unsuccessful.

Run 2: The starting material 9 for this run had been stored at −10° C. for approximately 3 months. TLC showed no degradation. Ethyl acetate (5.5L), methanol (600 mL), acetic acid (61 mL, 1.01 moles, 1 eq), and zinc (195 g, 3.01 moles, 3 eq) were added to a clean dry 22 L round bottom flask. The solution was stirred for 20 minutes. Compound 9 (615 g, 101 moles, 1 eq) was added in one portion and the temperature was maintained below 30° C. with an ice bath. TLC (9:1 ethyl acetate/methanol, UV & PMA visualization) showed the reaction was complete within 3 hours. The solution was then allowed to stir for 16 hours (overnight) at room temperature. The solids were filtered off and the filtrate was washed with 1×4 L water, 1×6 L 10% ammonium chloride and 1×6 L of a 10% potassium carbonate solution saturated with sodium chloride, and finally dried over sodium sulfate. After removing the drying agent, the solvent was removed under vacuum to yield 382 g (quantitative) of a tan solid. The solid was triturated with a 9:1 hexane/ethanol solution for 16 hours. The solids were isolated by filtration, washed with 500 mL of the above solution, and dried in a vacuum oven for 16 hours at 35° C. to yield 226 g (65%) of 10 as a tan powder. The purity was 95% by HPLC and $^1$H NMR confirmed structure with some impurities present. Elemental analysis indicated 8% ash content, which was removed by filtering through Celite® in the next step.

Preparation of β-L-FD4C 11

Two separate runs were performed as follows.

Run 1: Compound 10 prepared in Run 1 above (273 g, 0.79 moles, 1 eq) and anhydrous methanol (3 L) were combined in a clean, dry 22 L round bottom flask fitted with a mechanical stirrer, ice bath, temperature probe, and gas dispersion tube. While stirring and maintaining the temperature under 25° C., anhydrous ammonia gas was bubbled into the flask for 1 hour. The flask was then sealed and allowed to stir for 24 hours (overnight) at room temperature. TLC (9:1 ethyl acetate/methanol, PMA visualization) indicated that the reaction was complete. The solution was then filtered through Celite® and the filtrate was concentrated under vacuum to yield 180 g of a light solid. The solids were triturated with 2 L of ethyl acetate for 16 hours, isolated by filtration, and dried for 16 hours in a vacuum oven at 35° C. to yield 151 g (84%) of β-L-FD4C 11 as a white solid. The purity was 99.7% by HPLC. $^1$H NMR, $^{13}$C NMR, MS, elemental analysis, and optical rotation confirmed structure and purity of the compound.

Run 2: Compound 10 (226 g, 0.655 moles, 1 eq) and anhydrous methanol (3 L) were combined in a clean, dry 22 L round bottom flask. While stirring and maintaining the temperature below 25° C., anhydrous ammonia gas was bubbled into the solution for 1 hour. The flask was then sealed and allowed to stir for 24 hours (overnight). TLC indicated the reaction was complete, and the solution was filtered through Celite® to remove suspended insoluble material. The filtrate was then concentrated to a tan solid under vacuum. The solids were pulverized with a mortar and pestle and triturated with 3 L of ethyl acetate for 3 days (over the weekend). The solids were isolated by filtration, washed with 1 L of ethyl acetate, and dried for 16 hours in a vacuum oven at 35° C. to yield 147 g (98%) of β-L-FD4C 11 as a tan solid. The purity by HPLC was 96.5%. After some investigation, the 147 g of crude β-L-FD4C 11 were triturated with 10 mL/g of a 1:1 ethyl acetate/ethanol solution for 16 hours. The solids were isolated and dried to yield 105 g (70.6%) of β-L-FD4C 11 as a tan solid. HPLC indicated a purity of 98%. However, $^1$H NMR indicated some impurities, and elemental analysis indicated 8% ash content.

EXAMPLE 2

β-L-FD4C was prepared in a pilot plant according to the procedure outlined in FIG. 1, but employing several alternative solvents and reagents as described below. All weights and volumes are nominal unless otherwise stated. Input and output quantity, purity, and yield data are presented in Table 1 below.

Preparation of Acetal 3

A reaction vessel was charged with L-xylose 1 (1.0 wt, 1.0 mol eq) and acetone (7.9 wt, 10.0 vol). The resultant slurry was stirred vigorously and anhydrous copper sulfate (1.33 wt) was added while maintaining the reaction temperature below 25° C. Amberlyst® 15 resin (1.00 wt) was then added while maintaining the reaction temperature below 25° C. The resulting mixture was stirred vigorously at 20–25° C. until the reaction to form 2 was deemed complete by $^1$H NMR (<1 mol % L-xylose 1 remaining, typically about 16 hours).

The mixture was then filtered through Celite® and the filtrate transferred via a 1 μm filter to a second vessel. The filter cake was washed with acetone (2×1.58 wt, 2×2.0 vol) and the combined filtrates were transferred to a second vessel containing sodium carbonate (0.5 wt). The resulting mixture was stirred vigorously for 30–40 minutes, after which it was verified that the supernatant liquid in water had pH≧7. The mixture was then concentrated by vacuum distillation at up to 30° C. to ca 5 vol. Industrial methylated spirits (IMS, 2.02 wt, 2.5 vol) was then charged to the vessel and the resulting mixture was concentrated to ca 5 vol under vacuum at 25–30° C. A further portion of IMS (2.02 wt, 2.5 vol) was charged to the vessel and the resulting mixture was distilled under vacuum at 25–35° C. to ca 5 vol. The IMS charge and distillation was repeated once more. $^1$H NMR was used to verify that the sample contained less than 1 mol % of acetone with respect to ethanol. The mixture was then filtered and the filter cake washed with IMS (1.62 wt, 2.0 vol). The combined filtrate and wash were heated to 25–30° C., and a 1.2 M HCl solution (0.34 vol) was added while maintaining the reaction temperature at 25–30° C. The pH at this point was ≦1. The reaction mixture was stirred until deprotection to form compound 3 was deemed complete by $^1$H NMR (>94 mol % product 3, typically about 4 hours).

The resulting mixture was transferred to a separate vessel, which contained a slurry of sodium bicarbonate (1.0 wt) in IMS (1.61 wt, 2.0 vol), while maintaining the temperature at 20–30° C. The resulting mixture was stirred for 30–40 minutes, after which it was verified that the supernatant liquid in water had pH≧7. The mixture was concentrated by vacuum distillation at up to 35° C. to ca 4 vol. Toluene (4.31 wt, 5.0 vol) was then charged to the vessel, and the resulting mixture was concentrated to ca 4 vol in vacuo at 25–35° C. A further portion of toluene (4.31 wt, 5.0 vol) was charged to the vessel, and the vessel contents were concentrated to ca 4 vol total in vacuo at 25–35° C. $^1$H NMR was used to verify that the sample contained <1 mol % ethanol (IMS) with respect to toluene. Tertiary butyl methyl ether (TBME) (2.96 wt, 4.0 vol) was then charged to the vessel, and $^1$H NMR analysis was performed to verify that the toluene/TBME molar ratio was 1:1. The resultant mixture was stirred for 30–40 minutes before being filtered, and the filter cake was washed with TBME (1.48 wt, 2.0 vol).

Preparation of Diester 4

Dimethylaminopyridine DMAP (0.025 wt) was charged to a reaction vessel. The solution of acetal 3 (1.0 wt, 1.0 mol eq) in toluene/TBME (ca 10 vol total) prepared as described above was added to the vessel and stirred, followed by the addition of triethylamine (2.11 wt, 2.9 vol, 4.0 mol eq). TBME (0.74 wt, 1.0 vol) was then charged to the vessel as a line rinse. The mixture was cooled to 0–5° C. and p-toluoyl chloride (1.79 wt, 1.53 vol, 2.2 mol eq) was charged to the vessel while maintaining the temperature at 0–10° C. over a period of at least 30 minutes. The header tank was rinsed with TBME (0.74 wt, 1.0 vol) into the vessel. The mixture was then warmed to 20–25° C. over 30–40 minutes and stirred until the reaction to form compound 4 was deemed complete by HPLC (<0.5% by area mono-acylated intermediate, approximately 4 hours). A 3M HCl solution (4.0 vol) was charged to the vessel while maintaining the reactor contents at below 25° C., and it was verified that the aqueous phase had pH<1. The reaction mixture was then allowed to separate. The organic layer was washed with water (2×2.0 vol) and then sodium bicarbonate solution (1.0 vol). It was verified that the aqueous phase had pH>7. The organic phase was then washed with purified water (2×2.0 vol). After the washes were complete, the mixture was concentrated to ca 4.5 vol by vacuum distillation at 30–35° C.

Preparation of Diol 5

To a solution of the diester 4 (1.0 wt, 1.0 mol eq) in toluene from the previous step (ca 2 vol in total) was charged acetonitrile (1.57 wt, 2.0 vol) followed by purified water (1.0 vol) and formic acid (4.88 wt, 4.0 vol). The resulting two-phase mixture was heated to 40–45° C. and stirred until reaction to form the diol 5 was complete by HPLC analysis (<7% starting material 4; typically 12–16 hours).

The reaction mixture was cooled to 20–25° C. and charged with 30% w/w brine (3.0 vol) followed by TBME (0.74 wt, 1.0 vol). The layers were separated and the aqueous layer was washed with TBME (1.85 wt, 2.5 vol and 2.59 wt, 3.5 vol). The combined organic layers were washed with water (2×3.0 vol), then 1:1 brine:5% w/v sodium bicarbonate solution (4.0 vol), followed by 5% w/v sodium bicarbonate solution (2×3.0 vol), and finally purified water (3.0 vol). The resulting organic solution was concentrated to ca 4 vol by vacuum distillation at up to 35° C., and the water content was checked. If the water content was >3% w/w, toluene (3.46 wt, 4.0 vol) was added and removed by vacuum distillation at up to 35° C. The water content was rechecked and the toluene azeotrope repeated as necessary. The solution was then clarified, the filter rinsed with toluene (1.73 wt, 2.0 vol), and the solution concentrated to ca 2 vol by vacuum distillation at up to 35° C. The solution was adjusted to 30–35° C. as necessary, and isopropyl ether (IPE, 4.35 wt, 6.0 vol) was charged slowly, maintaining the temperature at 30–35° C. The resulting solution was cooled to 0–5° C. and aged for 3–4 hours, after which the solid was isolated by centrifugation. The solid cake was washed with IPE (2×1.45 wt, 2×2.0 vol), and the solid dried in vacuo at up to 35° C.

Preparation of Halogenated 5-Fluorocytosine Derivative 9

Glycal 6: Compound 6 was prepared as follows. Iodine (1.447 wt) and dichloromethane (DCM, 7.30 wt, 5.5 vol) were charged to a reaction vessel, followed by triphenylphosphine (1.50 wt) in DCM (5.84 wt, 4.4 vol), while maintaining the temperature at 20–30° C. A DCM (1.46 wt, 1.1 vol) line rinse was then performed. Imidazole (0.85 wt) in DCM (5.84 wt, 4.4 vol) was charged to the slurry while maintaining the temperature at 20–30° C. A DCM (1.46 wt, 1.1 vol) line rinse was performed and the slurry was cooled to 0–10° C. Compound 5 (1.00 wt, 1.0 mol eq) in DCM (5.84 wt, 4.4 vol) was added slowly while maintaining the temperature at <10° C., followed by a DCM (1.46 wt, 1.1 vol) line rinse. The resulting mixture was adjusted to 5–10° C. and stirred until the reaction to form 6 was complete by $^1$H NMR analysis (disappearance of 5, typically 30 minutes). The reaction mixture was unstable and began to degrade after 3 hours.

20% sodium thiosulfate solution (11.0 vol) was added to the reaction mixture while maintaining the temperature at <10° C., and the two-phase mixture was stirred vigorously at 5–10° C. for 15 minutes. The organic layer was tested for iodine content, the layers were separated, and the organic layer was washed with purified water (11.0 vol) at 5–10° C. Magnesium sulfate (0.55 wt) was charged to the organic phase and the mixture was stirred for 2 hours at 5–10° C. The dried solution was filtered and the solid was washed with DCM (2.92 wt, 2.2 vol). The resulting organic solution was concentrated down to ca 5 vol under vacuum at up to 20° C. and TBME (8.14 wt, 11.0 vol) was added. The solution was again concentrated to ca 5 vol and TBME (8.14 wt, 11.0 vol) added. The solution was again concentrated to ca 5 vol and $^1$H NMR was used to verify a TBME:DCM ratio ≧10:1. The solid was filtered off (ca 3 vol filter cake) and washed with TBME (2×1.63 wt, 2×2.2 vol). The water content of the combined filtrate was checked and it was concentrated to ca 2 vol at up to 20° C. DCM (7.30 wt, 5.5 vol) was added to the concentrate and the solution of 6 was held at <5° C. until use in the coupling step. The product 6 was unstable and began to degrade after 48 hours at >5° C.

Bis-protected 5-fluorocytosine 8: Compound 8 was prepared as follows. Wt/vol ratios refer to input weights of 5 in the preparation of 6 described above; mol eq are relative to 5-fluorocytosine 7. 5-Fluorocytosine 7 (0.4 wt) and ammonium sulfate (0.016 wt, 0.04 mol eq) were charged to a clean, dry vessel purged with nitrogen. Chlorobenzene (2.2 wt, 2.0 vol) was charged and the resulting suspension subjected to KF analysis (typically <0.01% w/w). Hexamethyldisilazane (1.08 wt, 1.42 vol, 2.17 mol eq) was added, and the resulting white slurry was heated to 110–115° C. and stirred at that temperature for 16 hours. The resulting clear colorless solution of bis-protected 5-fluorocytosine 8 was cooled to 25–30° C., analyzed by $^1$H NMR (typically 90–100 mol % di-silyl, 0–10 mol % mono-silyl), and held at ambient temperature until required for use in the coupling step.

Coupling: The coupling step was performed as follows. Wt/vol ratios refer to input weights of 5 in the preparation of 6 described above. A clean, dry vessel was employed. The TBME/DCM solution of 6 prepared above (ca 7.7 vol) was charged to the reaction vessel containing the chlorobenzene solution of 8 prepared above (ca 4.4 vol) while maintaining the temperature at <20° C. The solution was cooled to 0–10° C. and NIS (0.80 wt) was added in 5 equal portions over 50 minutes at <10° C. The reaction mixture was stirred at 5–10° C. until reaction to form 9 was deemed complete by $^1$H NMR analysis (typically 1 hour).

10% sodium thiosulfate solution (11.0 vol) was added to the reaction mixture while maintaining the temperature at <20° C., and the resulting two-phase mixture was clarified to remove suspended solids. The layers were then separated and the organic layer washed with purified water (7.7 vol). The organic layer was checked for iodine content and stirred with magnesium sulfate (1.1 wt) for 2 hours at 20–25° C. The dried organic layer was filtered and the solid washed with DCM (2.92 wt, 2.2 vol). Ethanol (8.64 wt, 11.0 vol) was added to the combined organics and the solution was cooled to 0–5° C. over 2 hours. The resulting solid was filtered off and washed with ethanol (2×1.73 wt, 2×2.2 vol), and the isolated product 9 was dried under vacuum at <20° C.

Preparation of Dideoxy, Didehydro Cytidine Derivative 10

Wt/vol ratios refer to input weights of 9, correcting for ethanol from the previous step. Zinc powder (0.33 wt) was charged to the vessel, followed by methyl acetate (3.5 vol), methanol (0.97 vol), and acetic acid (0.09 vol). The resulting gray slurry was stirred for 30 minutes before heating to 25–28° C. Compound 9 (1.0 wt) was dissolved in methyl acetate (4.5 vol) at 20–25° C. in a separate vessel and added to the zinc slurry slowly while maintaining the temperature at <30° C. (about 30–60 minutes). A line rinse of methyl acetate (1 vol) was performed at 25° C. The resulting reaction to form 10 was stirred at 25–30° C. for 1 hour before a sample was taken for HPLC analysis (confirm 9 <0.5% area). The reaction mixture was then filtered through cloth (filter cake=0.08 vol) and re-circulated to clarify. The filter cake was washed with 9:1 methyl acetate:methanol (2×1.0 vol) at 25–30° C. The combined filtrates were washed with 25% w/w ammonium chloride (5 vol) and the layers were separated. The aqueous layer was washed with 9:1 methyl acetate:methanol (3.0 vol) at 25° C. and the layers were separated. The combined organic layers were then washed with 1:1 brine (30% w/w):sodium carbonate (20% w/w) (5 vol, pre-mixed) and the layers were separated. The aqueous layer was washed with 9:1 methyl acetate:methanol (3.0 vol) at 25° C. and the layers were separated. The combined organic layers were dried over magnesium sulfate (1.0 wt). The dried solution was filtered, the filter cake was washed (displacement) with 9:1 methyl acetate:methanol (2×2.0 vol) at 25–30° C., and the combined filtrates were distilled to 3 vol at up to 30° C. Acetone (4 vol) was added, and the resulting solution was distilled to 3 vol at up to 30° C. This cycle was repeated until the methanol content was <4 mol % with respect to acetone. The resulting white slurry was then cooled to 0–5° C. and aged for 1–2 hours before being filtered. The filter cake was washed with acetone at 0–5° C. (2×2 vol) and dried in vacuo at up to 35° C.

Preparation of β-L-FD4C 11

Wt/vol ratios refer to input weights of 10. Compound 10 (1.0 wt) was charged to a vessel, followed by methanol (10.0 vol). The resulting slurry was stirred, and ammonia (6 M in methanol, 5 vol) was added. The mixture was then heated to 30–35° C. and stirred vigorously until reaction to form β-L-FD4C 11 was complete by HPLC (typically 24–32 hours). The temperature was adjusted to 45–50° C. and the solution was clarified, followed by a 1 vol methanol line rinse at 45–50° C. Isopropyl alcohol (IPA, 15 vol) was added to the mixture. The resulting mixture was then distilled under reduced pressure at up to 35° C. until the IPA/methanol molar ratio was between 1.5:1 and 2:1 (at around 15–20 vol in the reaction vessel). The resulting white slurry was cooled to 0–5° C. and filtered, the filter cake was washed with IPA (2×2 vol), and the product β-L-FD4C 11 was dried in vacuo at up to 35° C.

TABLE 1

| Synthetic Step* | Input | | | Output | | | Yield | |
|---|---|---|---|---|---|---|---|---|
| | Batch | Weight (kg) | Purity (LC area %) | Batch | Weight (kg) | Purity (LC area %) | % th | % w/w |
| 1 → 3 | A | 50 | 99.78 | C | 53.4 | — | 84.3 | 107 |
| | B | 50 | | D | 45.76 | — | 73.3 | 91.5 |
| | B1 | | 99.94 | | | | | |
| | B2 | | 99.95 | | | | | |
| | B3 | | 99.78 | | | | | |
| | B4 | | 99.68 | | | | | |
| 3 → 5** | C | 53.4 | — | E | 50.58 | 96.2 | 46.6 | 94.7 |
| | D | 45.76 | — | F | 60.7 | 98.17 | 65.3 | 132.6 |
| 5 → 9 | E | 50.58 | 96.2 | G | 57.7 | 99.58 | 72.3 | 114.1 |
| | F | 58.6 | 98.17 | H | 48.42 | 99.21 | 52.8 | 82.6 |

TABLE 1-continued

| | Input | | | Output | | | |
|---|---|---|---|---|---|---|---|
| Synthetic | | Weight | Purity | | Weight | Purity | Yield |
| Step* | Batch | (kg) | (LC area %) | Batch | (kg) | (LC area %) | % th | % w/w |
| 9 → 10 | G + H | 80 | | I | 20.94 | 98.93 | 46 | 26.2 |
| | G | 36.76 | 99.58 | | | | | |
| | H | 43.24 | 99.21 | | | | | |
| 10 → 11 | I | 20.94 | 98.93 | J | 11.4 | 99.76 | 82.7 | 54.4 |

*Refer to compound conversions using the reference numbers in FIG. 1.
**The yield for compound 4 was assumed to be 100% th, so the overall yield was reported from compound 3 to compound 5.

While the foregoing invention has been described in some detail for purposes of clarity and understanding, it will be appreciated by one skilled in the art from a reading of this disclosure that various changes in form and detail can be made without departing from the scope of the invention.

What is claimed is:

1. A method of synthesizing β-L-5-fluoro-2',3'-dideoxy-2',3'-didehydrocytidine (β-L-FD4C), the method comprising:

(a) reacting L-xylose of formula I

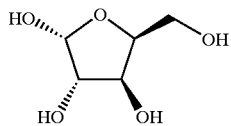

with acetone in the presence of a first acid catalyst and a dehydrating agent to afford a diacetal of formula II

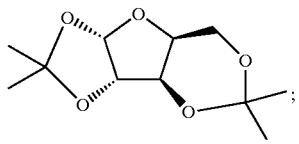

(b) hydrolyzing the 2,3 acetal of the diacetal of formula II in the presence of a second acid catalyst to afford an acetal of formula III

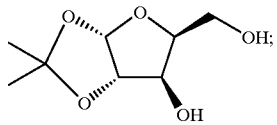

(c) acylating the alcohol moieties of the acetal of formula III in the presence of a base catalyst to afford a diester of formula IV

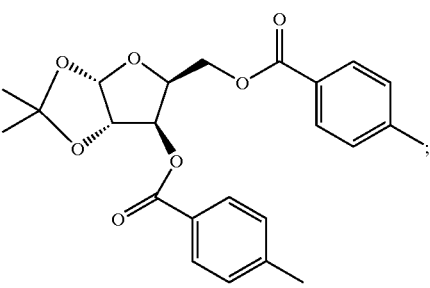

(d) hydrolyzing the acetal moiety of the diester of formula IV in the presence of an acid to afford a diol of formula V

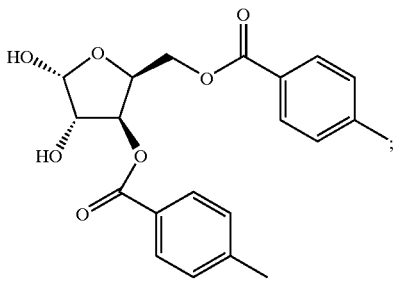

(e) removing the hydroxyl groups of the diol of formula V to afford a glycal of formula VI

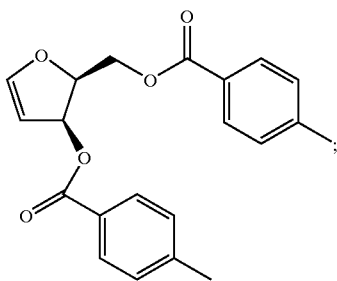

(f) bis-protecting 5-fluorocytosine of formula VII

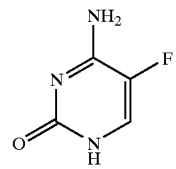

VII to afford bis-protected 5-fluorocytosine of formula VIII

VIII wherein Z is a protecting group;

(g) coupling the glycal of formula VI with the bis-protected 5-fluorocytosine of formula VIII in the presence of a halogenating agent to afford a halogenated cytosine derivative of formula IX

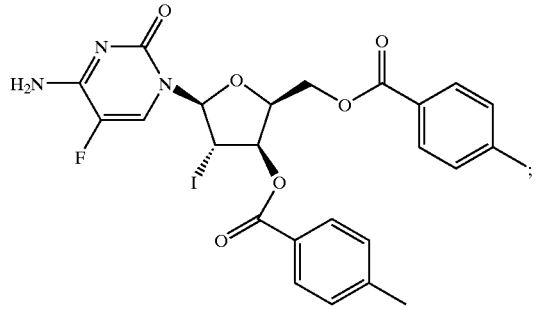

IX (h) treating the halogenated cytosine derivative of formula IX with metallic zinc and acetic acid to afford a dideoxy, didehydro cytidine derivative of formula X

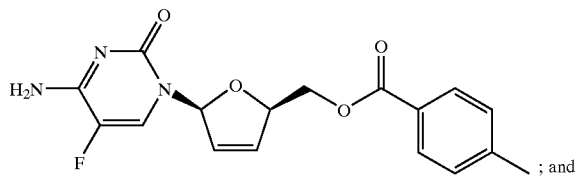

X

; and (i) hydrolyzing the ester moiety of the dideoxy, didehydro cytidine derivative of formula X in the presence of a base to afford β-L-5-fluoro-2',3'-dideoxy-2',3'-didehydrocytidine (β-L-FD4C) of formula XI

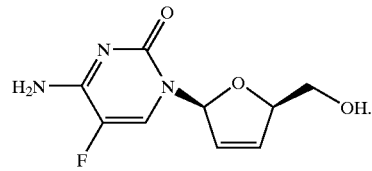

XI

2. The method of claim 1, further comprising isolating the product β-L-5-fluoro-2',3'-dideoxy-2',3'-didehydrocytidine (β-L-FD4C).

3. The method of claim 2, wherein isolating comprises treatment with a solvent that causes precipitation of β-L-5-fluoro-2',3'-dideoxy-2',3'-didehydrocytidine (β-L-FD4C).

4. The method of claim 3, wherein the solvent is ethyl acetate or isopropanol.

5. The method of claim 1, wherein removing the hydroxyl groups in step (e) comprises treatment with iodine, triphenylphosphine, and imidazole.

6. The method of claim 1, wherein bis-protecting in step (f) comprises treatment with 1,1,1-3,3,3-hexamethyldisilizane and a catalyst.

7. The method of claim 6, wherein the catalyst is ammonium sulfate.

8. The method of claim 1, wherein the protecting group Z at each occurrence in formula VIII is trimethylsilyl.

9. The method of claim 1, wherein the first and second acid catalysts in steps (a) and (b) are independently selected from the group consisting of sulfuric acid, hydrochloric acid, and cation exchange resins.

10. The method of claim 1, wherein the dehydrating agent in step (a) is selected from the group consisting of copper sulfate, magnesium sulfate, and sodium sulfate.

11. The method of claim 1, wherein the base catalyst in step (c) is selected from the group consisting of pyridine, triethylamine, dimethylaminopyridine, and combinations thereof.

12. The method of claim 1, wherein the acid in step (d) is formic acid or trifluoroacetic acid.

13. The method of claim 1, wherein the base in step (i) is selected from the group consisting of ammonia, sodium methoxide, potassium carbonate, 1,8-diazabicyclo[5.4.0]undec-7-ene (DBU), and isopropylamine.

14. The method of claim 1, wherein the halogenating agent in step (g) is N-iodosuccinimide (NIS).

15. The method of claim 1, wherein step (b) is performed in a lower alkyl alcohol solvent.

16. The method of claim 1, wherein step (c) is performed in a solvent selected from the group consisting of dichloromethane, toluene, tertiary butyl methyl ether, and combinations thereof.

17. The method of claim 1, wherein step (d) is performed in a solvent selected from the group consisting of acetonitrile, toluene, and combinations thereof.

18. The method of claim 1, wherein step (e) is performed in dichloromethane.

19. The method of claim 1, wherein step (f) is performed in a solvent selected from the group consisting of toluene, chlorobenzene, chloroform, dichloroethane, dichloromethane, isopropyl ether, and combinations thereof.

20. The method of claim 1, wherein step (g) is performed in a solvent selected from the group consisting of dichloromethane, dichloroethane, chlorobenzene, and combinations thereof.

21. The method of claim 1, wherein step (h) is performed in the presence of a lower alkyl alcohol and a lower alkyl acetate.

22. The method of claim 1, wherein step (i) is performed in methanol.

23. The method of claim 1, wherein synthesis of β-L-5-fluoro-2',3'-dideoxy-2',3'-didehydrocytidine (β-L-FD4C) is achieved from L-xylose without evaporation to dryness of any of the intermediate compounds of formulae II–X.

* * * * *